United States Patent
Tokuda et al.

(10) Patent No.: US 7,968,833 B2
(45) Date of Patent: Jun. 28, 2011

(54) IMAGE SENSOR WITH OPTICAL AND ELECTRICAL MEASUREMENT FUNCTIONS

(75) Inventors: Takashi Tokuda, Kyoto (JP); Jun Ohta, Soraku-gun (JP)

(73) Assignee: National University Corporation Nara Institute of Science and Technology, Ikoma (JP)

( * ) Notice: Subject to any disclaimer, the term of this patent is extended or adjusted under 35 U.S.C. 154(b) by 298 days.

(21) Appl. No.: 12/226,687

(22) PCT Filed: Apr. 12, 2007

(86) PCT No.: PCT/JP2007/000401
§ 371 (c)(1),
(2), (4) Date: Oct. 24, 2008

(87) PCT Pub. No.: WO2007/129451
PCT Pub. Date: Nov. 15, 2007

(65) Prior Publication Data
US 2009/0166514 A1     Jul. 2, 2009

(30) Foreign Application Priority Data

Apr. 26, 2006   (JP) .................................. 2006-121393

(51) Int. Cl.
*H01L 31/042* (2006.01)
(52) U.S. Cl. ...................... 250/208.1; 360/324; 257/448
(58) Field of Classification Search ............... 250/208.1; 360/324; 257/448
See application file for complete search history.

(56) References Cited

U.S. PATENT DOCUMENTS

2006/0014151 A1   1/2006   Ogura et al.
2007/0127164 A1*  6/2007   Ofek et al. ..................... 360/324

FOREIGN PATENT DOCUMENTS

| JP | A-2002-202303 | 7/2002 |
| JP | A-2004-205340 | 7/2004 |
| JP | A-2005-227155 | 8/2005 |
| JP | A-2005-252743 | 9/2005 |
| JP | A-2006-004991 | 1/2006 |
| WO | WO 2004/059006 A1 | 7/2004 |

OTHER PUBLICATIONS

Yamamoto et al., "Optical and potential dual-image CMOS sensor for on-chp DNA micro-array analysis," *ITE Technical Report*, vol. 29, No. 62, Oct. 28, 2005, pp. 1-4.

(Continued)

*Primary Examiner* — Seung C Sohn
(74) *Attorney, Agent, or Firm* — Oliff & Berridge, PLLC (57) ABSTRACT

The uppermost metallic wiring layer in light-blocking layers constituted by multilevel metallic wiring that prevents light from impinging on areas other than the light-receiving area of a photodiode in each picture cell is used as a measurement electrode to be directly contacted with a specimen to measure electrical signals. Furthermore, in each picture cell including a circuit for reading out electrical signals collected through the measurement electrode, another circuit for reading out electrical signals generated by the photodiode is provided in an independent or shared form. This configuration enables the photodiode for optical measurements and the measurement electrode for electrical measurements to be provided in every picture cell. Thus, in a hybrid image sensor having an optical measurement function for obtaining optical information due to specimen and an electrical measurement functions for obtaining electrical information due to the specimen, the spatial resolution of both types of two-dimensional images can be simultaneously improved.

17 Claims, 6 Drawing Sheets

OTHER PUBLICATIONS

Yamamoto et al., "DNA spots imaging using an optical and potential dual-image CMOS sensor," *The Japan Society of Applied Physics and Related Sciences*, vol. 3, Mar. 22, 2006, pp. 1382 (25a-I-4).

Tanaka et al., "A Multi-Functional CMOS Image Sensor with On-Chip Multi-site Electrochemical Sensing Function," *The Institute of Image Electronics Engineers*, Nov. 14, 2005, pp. 31-34.

* cited by examiner

IMAGE SENSOR WITH OPTICAL AND ELECTRICAL MEASUREMENT FUNCTIONS

TECHNICAL FIELD

The Present invention relates to an image sensor for detecting optical and electrical information originating from a specimen (i.e. an object to be measured) and for reproducing a two-dimensional image associated with the measured sample. More specifically, it relates to an image sensor suited for measuring or observing various kinds of biomedical substance such as DNA, mRNA, proteins, peptides or sugars, mainly in the fields of biochemistry, molecular biology, clinical medicine and so on.

BACKGROUND ART

Genetic information regarding living organisms has been recently expanding its applications in biochemistry, molecular biology, clinical medicine and other technical fields, and this trend has promoted rapid progress in the techniques for the structural analysis of DNA. A conventional method for analyzing DNA structures uses DNA microarrays, which may also be called DNA microchips. A DNA microarray consists of a slide glass or similar substrate on which DNA probes with known base sequences of different patterns are fixed. When a sample DNA as a specimen is supplied onto the substrate, the sample DNA complimentarily combines with a corresponding, specific DNA probe due to hybridization and is thereby fixed on the substrate. Accordingly, it is possible to obtain information about the base sequence of the sample DNA by locating the DNA probe which has been combined with the sample DNA.

The methods for locating a DNA probe combined with a sample DNA can be broadly divided into two types; the type that employs an optical measurement, and the type that employs an electrical measurement. In the former type of method, a sample DNA that has been fluorescently labeled is supplied onto the microarray substrate and made to combine with a DNA probe. In this state, a ray of excitation light with a predetermined wavelength is cast onto the microarray. As a result, only the DNA probe that has combined with the sample DNA produces fluorescence. Accordingly, it is possible to obtain information about the base sequence of the sample DNA by detecting the intensity of the fluorescence with a photo detector and determining which DNA probe is producing the fluorescence. This method generally requires an apparatus capable of detecting a faint fluorescence, e.g. a near-field microscope. However, some conventionally proposed apparatuses have a two-dimensional detector integrated with a DNA microarray (for example, refer to Patent Documents 1 and 2).

Integration of a DNA microarray with a detection sensor has also been attempted in the electrical measurement. One of the conventionally proposed methods uses an electrode being directly in contact with a target spot of a specimen to detect a change in its electrochemical characteristics due to hybridization. Another method uses an electrode being capacity-coupled with the target spot via an insulator film or similar device to detect a change in the electrostatic characteristics of that spot.

In the structural analysis of DNA by means of a DNA microarray, if the detection by the optical measurement and the detection by the electrical measurement can be concurrently performed, it is expected that the omission and uncertainty of the two detection methods will be compensated, so that the analytical accuracy will significantly improve. However, no conventional sensor has been capable of realizing such a hybrid analysis.

The simultaneous performance of the optical and electrical measurements is very effective not only in the analysis using a DNA microarray; it is generally effective in the observation or measurement of biological samples, such as biomedical substances. From this viewpoint, the inventors have proposed an image sensor capable of simultaneously performing an optical measurement and electrical measurement of a biological sample, as disclosed in Patent Document 3. The image sensor described in this document has a two-dimensional array of photoelectric conversion units in each of which picture elements are partially replaced by an electrode protruding upward from a protective film. This electrode is designed to some in contact with a sample placed on the protective film, thus making it possible to extract electric signals of the sample while simultaneously detecting a fluorescence or similar light emitted from the sample with the photoelectric conversion unit.

This configuration is premised on the idea that the electrical measurement is no more than a supplemental measure. Therefore, increasing the number of electrodes to enhance the spatial resolution of the two-dimensional image obtained by the electrical measurement inevitably decreases the number of photoelectric conversion units and accordingly lowers the spatial resolution of the two-dimensional image obtained by the optical measurement. Thus, the spatial resolutions of the two types of two-dimensional images cannot be simultaneously improved, so that it is difficult to always obtain results that can be complementarily used.

Patent Document 1: Japanese Unexamined Patent Application Publication No. 2002-202303

Patent Document 2: Japanese Unexamined Patent Application Publication No. 2006-4991

Patent Document 3: Japanese Unexamined Patent Application Publication No. 2005-227155

DISCLOSURE OF THE INVENTION

Problem to be Solved by the Invention

The present invention has been developed in view of these problems, and its first objective is to provide an image sensor capable of acquiring both a high-resolution two-dimensional image by an optical measurement of a fluorescence or similar light and a high-resolution two-dimensional image by an electrical measurement in a concurrent or time-sharing manner for the same sample.

In putting such an image sensor into practice, it is necessary to apply large-scale integration (LSI) techniques to the manufacture of a measurement electrode for the electrical measurement. Unfortunately, the aforementioned capacity-coupling configuration may cause an accumulation of residual charges during the LSI manufacturing process, which will later become background noise.

Thus, the second objective of the present invention is to provide an image sensor capable of easily removing those residual charges and thereby preventing the background noise.

Furthermore, the third objective of the present invention is to provide an image sensor in which LSI technologies are applied so as to enable sophisticated measurements that could not have been achieved by conventional electrical measurements.

Means for Solving the Problems

To achieve the first objective, a first aspect of the present invention provides an image sensor having a semiconductor substrate on which both an optical measurement function for obtaining optical information originating from a specimen and an electrical measurement function for obtaining electrical information due to the specimen via a direct contact or capacity-coupling with the specimen are mounted, including:

a) a photoelectric conversion unit for the optical measurement function, located in the surface layer of the semiconductor substrate;

b) a plurality of light-blocking layers covering the surface layer of the semiconductor substrate, at least the uppermost layer thereof being an electrically conductive layer having a non-light-blocking area for introducing light into the photoelectric conversion unit; and c) measurement electrodes for the electrical measurement function, created by utilizing the uppermost electrically conductive layer of the light-blocking layers.

The electrically conductive layer is typically a metallic layer. However, it may be made of another electrically conductive material other than metals.

In a preferable mode of the image sensor according to the first aspect of the present invention, a large number of picture cells are arrayed in a two-dimensional pattern with n rows and m columns on one side of the semiconductor substrate, each picture cell including a first readout circuit for selectively reading out an electric signal obtained by the photoelectric conversion unit and a second readout circuit for reading out an electric signal obtained by the measurement electrode, in addition to the photoelectric conversion unit and the measurement electrode. The photoelectric conversion unit is typically a photodiode.

LSI circuits used in complimentary metal-oxide-silicon (CMOS) image sensors or the like generally include a multilevel interconnection with two or more layers. These metallic wiring layers, which are formed on the semiconductor substrate for the sake of the multilevel interconnection, can be used as the light-blocking layers. Other layers such as a polycrystalline silicon layer for creating the gate electrode of a metal-oxide-silicon (MOS) transistor or a condenser may also be present in addition to the metallic wiring layers. The minimum requirement is that the uppermost light-blocking layer is an electrically conductive layer made of a type of metal or other appropriate materials.

The light-blocking layers are basically intended for preventing the generation of unnecessary electric charges due to an incidence of light into components other than tie photoelectric conversion unit, such as the MOS transistor constituting a readout circuit. In these layers, the light-blocking and non-light-blocking areas are defined by appropriately designing the pattern of the multilevel interconnection. In the image sensor according to the first aspect of the present invention, the uppermost electrically conductive layer of the light-blocking layers is divided into sections corresponding to, for example, the picture cells, and each section is utilized as a measurement electrode. The portions where the electrically conductive layer has been removed to divide the layer corresponding to the picture cells lose their light-blocking function. This functional loss should preferably be compensated by, for example, carefully designing the patterns of metallic wires or other components at the lower layers so that light will be blocked at those portions.

Effects of the Invention

In the image sensor according to the first aspect of the present invention, each picture element can have one measurement electrode together with one photoelectric conversion unit, so that a high spatial resolution can be ensured for both the two-dimensional image capturing an optical phenomenon based on electric signals produced by the photoelectric conversion unit and the two-dimensional image capturing an electrical phenomenon based on electric signals collected through the measurement electrode. The two types of two-dimensional images can be acquired in a concurrent or time-sharing manner. Therefore, it is possible to appropriately combine the optical information and electrical information or compensate one of the two kinds of information with the other so that a target object can be observed or measured with a significantly improved accuracy.

The image sensor according to the first aspect of the present invention may have a protective film layer provided on the surface of the light-blocking layers. In this case, the measurement electrode has two mode options. In one mode, the protective film layer is formed on the surface of the light-blocking layers, and an opening is formed in the protective film layer above the measurement electrode so as to expose the measurement electrode. In this mode, the measurement electrode can contact the specimen to directly measure electric signals. In the other mode, the measurement electrode is covered with an insulating protective film layer so that the measurement electrode is unexposed. In this case, it is possible to measure electric signals generated in the measurement electrode by capacity-coupling this electrode to the specimen on the protective film layer with the protective film layer in between.

Thus, the electrical measurement mode can be selected between the direct measurement and capacity-coupling measurement by choosing whether to remove the protective film layer covering the measurement electrode. It is naturally possible to create a hybrid image sensor in which a predetermined number of picture cells are designed to operate in the direct measurement mode and other picture cells in the capacity-coupling measurement mode.

In the image sensor according to the first aspect of the present invention, it is possible that the first readout circuit for the optical measurement and the second readout circuit for the electrical measurement are separately provided for each picture cell, and a signal readout line shared by a plurality of picture cells arranged in a row is separately provided for each of the optical and electrical measurements. This configuration enables the optical and electrical measurements to be performed simultaneously.

It is also possible that at least a portion of the first readout circuit is shared with the second readout circuit in each picture cell, and a signal readout line shared by a plurality of picture cells arranged in a row is used in both the optical and electrical measurements. This configuration makes it possible to miniaturize the picture cell and thereby increase the density of the picture cells, although the simultaneous measurement cannot be completely performed.

To achieve the second objective, a second aspect of the present invention provides an image sensor for obtaining a two-dimensional image obtained from an electrical phenomenon of a specimen, including:

a plurality of measurement electrodes arrayed in a two-dimensional pattern with n rows and m columns, for collecting electric signals due to the specimen via capacity-coupling;

a MOS transistor circuit provided for each measurement electrode, for reading out an electric signal collected through the measurement electrode; and a MOS transistor circuit provided for each measurement electrode, for resetting a potential accumulated in the measurement electrode.

In the image sensor according to the second aspect of the present invention, each measurement electrode can be reset to a predetermined potential via the resetting MOS transistor circuit, whereby the electric charges that have been accumulated at the junctions or other portions near the measurement electrode during an LSI manufacturing process or other processes can be easily removed. As a result, the background noise due to the residual charges will be reduced and the precision of resultant two-dimensional images will be improved.

It is naturally possible to introduce the components of the second aspect of the present invention into the image sensor according to the first aspect of the present invention. This ensures a high spatial resolution for both the two-dimensional image capturing an optical phenomenon based on the electric signals produced by the optical conversion unit and the two-dimensional image capturing an electrical phenomenon based on the electric signals collected through the measurement electrode, and also improves the accuracy of the latter type of two-dimensional image.

To achieve the third objective, a third aspect of the present invention provides an image sensor for obtaining a two-dimensional image obtained from an electrical phenomenon of a specimen, including:

a plurality of measurement electrodes arrayed in a two-dimensional pattern with n rows and m columns, for collecting electric signals due to the specimen via a direct contact with the specimen;

a readout MOS transistor circuit provided for each measurement electrode, for reading out an electric signal collected through the measurement electrode;

a current-injection MOS transistor circuit provided for each measurement electrode, for supplying an electric current into the specimen via the measurement electrode; and a current supply circuit and a current supply line which are separately provided for each column where the current supply line is connected to the current-injection MOS transistor circuits corresponding to a plurality of measurement electrodes arranged in a column.

With the image sensor according to the third aspect of the present invention, it is possible, for example, to measure a local potential change of a specimen via the readout MOS transistor circuit while supplying a predetermined electric current to the specimen through the current-injection MOS transistor circuit or controlling the current level. It is also possible to measure an electric current locally flowing through a specimen while applying a predetermined voltage to the specimen. Thus, various measurements can be performed with an electric current as a controlled variable and a voltage as a measured quantity, or vice versa.

It is naturally possible to introduce the components of the third aspect of the present invention into the image sensor according to the first aspect of the present invention. This ensures a high spatial resolution for both the two-dimensional image capturing an optical phenomenon based on the electric signals produced by the optical conversion unit and the two-dimensional image capturing an electrical phenomenon based on the electric signals collected through the measurement electrode, and also enables the measurement electrodes to be used for performing various measurements with an electric current as a controlled variable and a voltage as a measured quantity, or vice versa.

EXPLANATION OF NUMERALS

1 . . . Image Cell Section
2 . . . Row Scanner
3 . . . Column Circuit Section
4 . . . Output Circuit Section
5 . . . Column Scanner
6 . . . Timing Control Circuit
7 . . . Output Terminal
10 . . . Picture Cell
10a . . . Optical Measurement Section
10b . . . Electrical Measurement Section
11 . . . Photodiode
12, 13, 14, 16, 17, 18, 40, 41, 42, 43, 50, 51 . . . MOS transistor
15 . . . Measurement Electrode
20 . . . Optical Measurement Reset Signal Line
21 . . . Electrical Measurement Reset Signal Line
22 . . . Voltage Signal Line
23 . . . Row Selection Signal Line
24 . . . Column Reset Signal Line
25 . . . Optical Measurement Output Signal Line
26 . . . Electrical Measurement Output Signal Line
27 . . . Optical Measurement Selection Signal Line
28 . . . Electrical Measurement Selection Signal Line
30 . . . Silicon Substrate
31 . . . Circuit Section
32, 321-324 . . . Metallic Wiring layers
33 . . . Interlayer Dielectric
34 . . . Protective Film Layer
35 . . . Opening
36 . . . Window Opening
43 . . . Switch Section
44 . . . I/V conversion amplifier
45 . . . Switch Section
46 . . . Resistor Section

BEST MODE FOR CARRYING OUT THE INVENTION

First Embodiment

Figure 1:
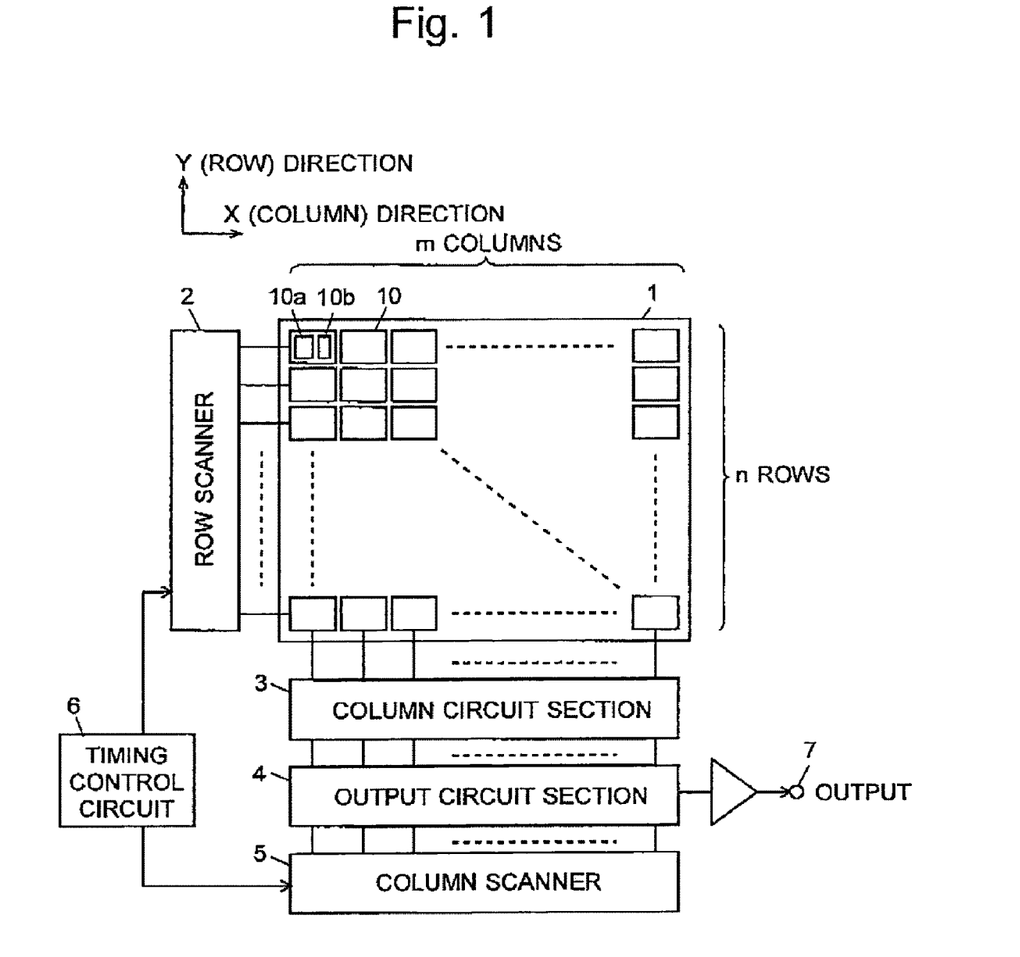
FIG. 1 is a block diagram showing the overall configuration of an image sensor according to an embodiment (first embodiment) of the present invention.
Figure 2:
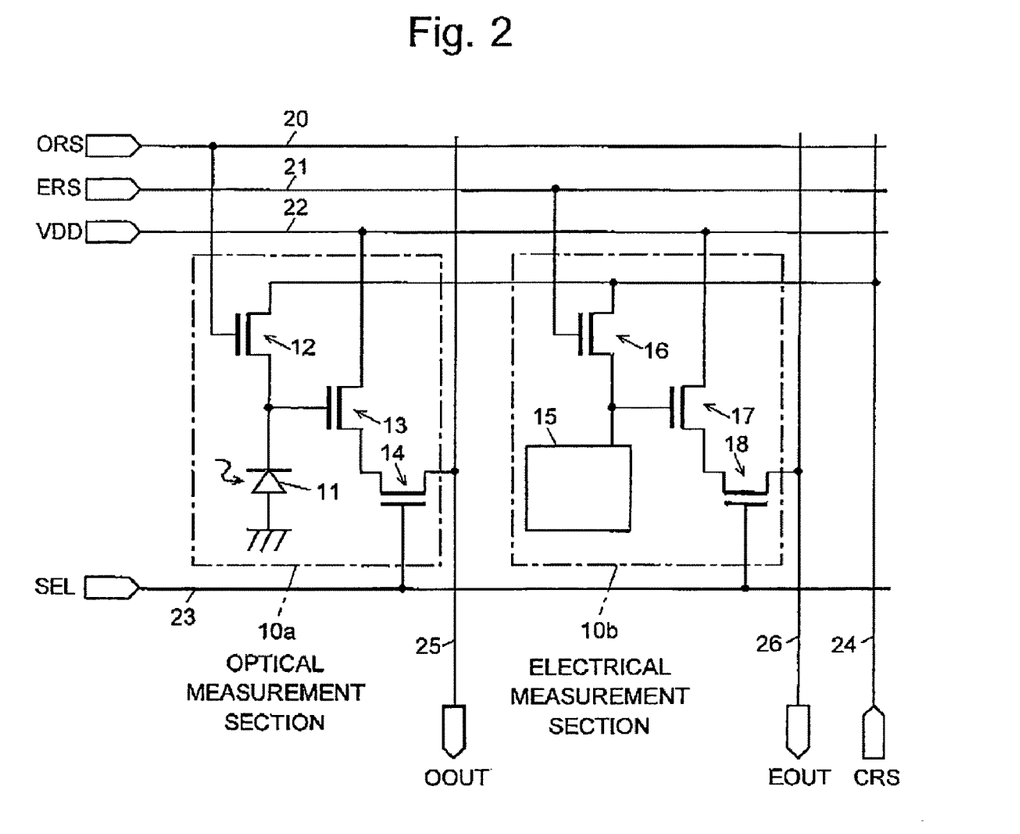
FIG. 2 is a circuit configuration diagram of one picture cell in the image sensor of the first embodiment.
Figure 3:
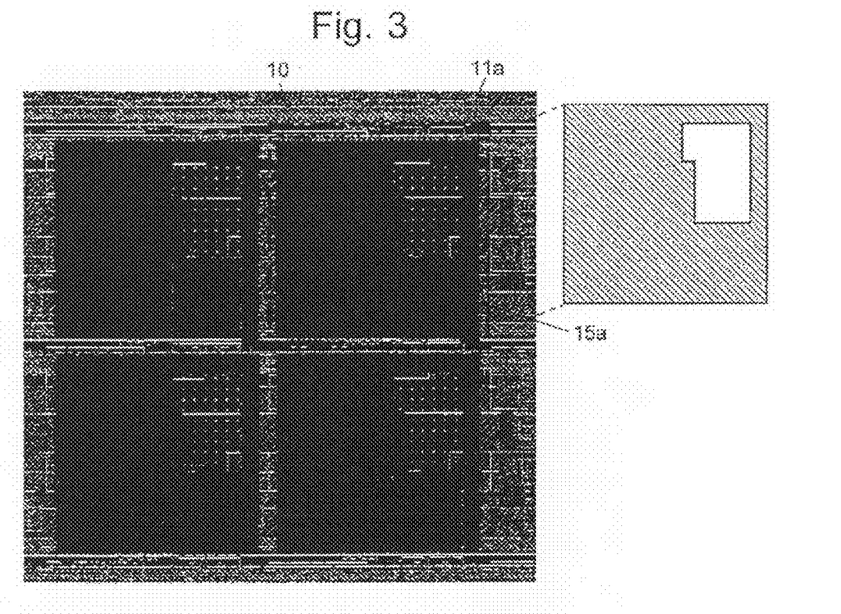
FIG. 3 is a plan view showing a picture-element layout in the image sensor of the first embodiment.
Figure 4:
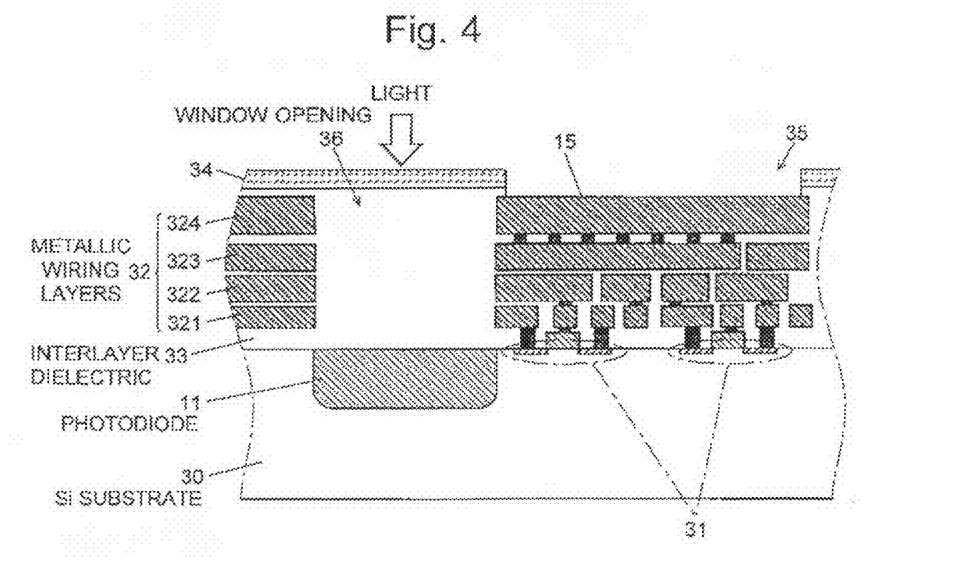
FIG. 4 is a schematic vertical sectional view of one picture cell in the image sensor of the first embodiment.
Figure 5:
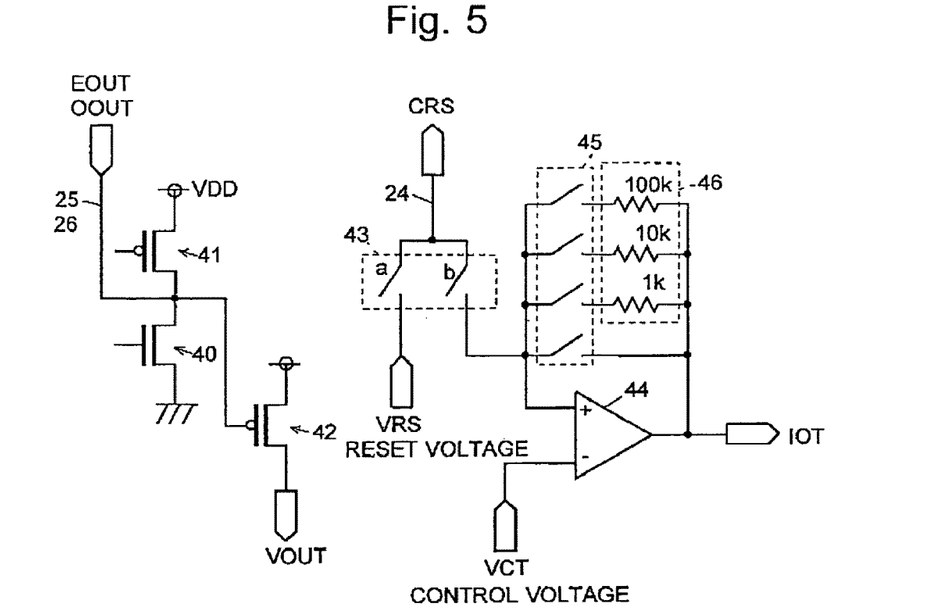
FIG. 5 is a configuration diagram of a column circuit in the image sensor of the first embodiment.

An embodiment of the image sensor according to the present invention (which is hereinafter called the first embodiment) is described with reference to the attached drawings, where FIG. 1 is a block diagram showing the overall configuration of the image sensor in the present embodiment, FIG. 2 is a circuit configuration diagram of one picture cell, FIG. 3 is a plan view showing a picture-element layout, FIG. 4 is a schematic vertical sectional view of one picture cell, and FIG. 5 is a configuration diagram of a column circuit provided for each column.

As shown in FIG. 1, the image sensor in the present embodiment includes: an image cell section 1 having picture cells 10 arranged in a two-dimensional array pattern with n rows and m columns; a row scanner 2 for setting various control signals for m pieces of picture cells 10 constituting each row of the image cell section 1; a column circuit section 3 provided for each column of the image cell section 1; an output circuit section 4 for converting parallel signals obtained by the column circuit section 3 for each column to serial signals and outputting these signals; a column scanner 5 for setting various control signals for n pieces of picture cells 10 constituting each column of the image cell section 1; and a liming control circuit 6 for supplying predetermined control signals to the these sections. Each picture cell 10 has an optical measurement section 10a for collecting optical information from a target object and an electrical measurement section 10b for collecting electrical information.

In the image sensor of the first embodiment, the optical measurement section 10a and the electrical measurement section 10b in each picture cell 10 are separately provided, as shown in FIG. 2. The optical measurement section 10a consists of one photodiode 11 and three MOS transistors 12, 13 and 14. The electrical measurement section 10b consists of one measurement electrode 15 and three MOS transistors 16, 17 and 18. The electrical measurement section 10b is structurally identical to the optical measurement section 10a except that the photodiode 11 is replaced by the measurement electrode 15.

In the optical measurement section 10a, the photodiode 11 has its anode terminal grounded, while its cathode terminal is connected to the source terminal of the first MOS transistor 12 used for a resetting operation and gate terminal of the second MOS transistor 13 functioning as a source follower amplifier. The gate and drain terminals of the first MOS transistor 12 are respectively connected to an optical measurement reset signal line 20 and a column reset signal line 24. The second MOS transistor 13 has its drain terminal connected to a voltage signal line 22, while its source terminal is connected to an optical measurement output signal line 25 via the third MOS transistor 14 functioning as an output selector switch. The gate terminal of the third MOS transistor 14 is connected to a row selection signal line 23.

In the electric measurement section 10b, the measurement electrode 15 is connected to the source terminal of the fourth MOS transistor 16 and the gate terminal of the fifth MOS transistor 17 functioning as a source follower amplifier. The gate and drain terminals of tie fourth MOS transistor 16 are respectively connected to an electric measurement reset signal line 21 and the column reset signal line 24. The fifth MOS transistor 17 has its drain terminal connected to the voltage signal line 22, while its source terminal is connected to an electric measurement output signal line 26 via the sixth MOS transistor 18 functioning as an output selector switch. The gate terminal of the sixth MOS transistor 18 is connected to the row selection signal line 23.

The optical measurement reset signal line 20, electrical measurement reset signal line 21 and row selection signal line 23 are shared by m pieces of picture cells 10 belonging to the same row in the image cell section 1. The column reset signal line 24, optical measurement output signal line 25 and electrical measurement output signal line 26 are shared by n pieces of picture cells 10 belonging to the same column in the image cell section 1. These picture-element configurations are basically identical to those of the generally used conventional image sensors.

As just described, in the image sensor of the present embodiment, the photodiode 11 as the photoelectric conversion unit and the measurement electrode 15 for the electrical measurement are provided in each picture cell 10. Its picture-element has a characteristic structure for including the measurement electrode 15. Specifically, as shown in FIG. 3, each picture cell 10 has a light-receiving area 11a of the photodiode 11 and a surrounding area 15a that is broadly occupied by the measurement electrode 15. The areas 15a occupied by the measurement electrodes 15 in the neighboring picture cells 10 are separated in a grid pattern.

As shown in FIG. 4, a circuit section 31 is provided on the surface of a semiconductor substrate 30, which is made of silicon. The circuit section includes a photodiode 11, a MOS transistor for reading out signals produced by the photodiode 11, and another MOS transistor for reading out signals collected through the measurement electrode 15. Located on this circuit section are four-level metallic wiring layers 32, with an interlayer dielectric 33 made of $SiO_2$ or other materials in between. The uppermost layer of the metallic wiring layers 32 is covered by a protective film layer 34. The metallic wiring layers 32 include, in order of formation, a first metallic wiring layer 321, second metallic wiring layer 322, third metallic wiring layer 323 and fourth metallic wiring layer 324. Mostly, the first and second metallic wiring layers 321 and 322 are used for providing signal wires inside a circuit or between circuits, while the third and fourth metallic wiring layers 323 and 324 are designed in a roughly solid pattern and used for a power simply or grounding.

The metallic wires block light, but the photodiode 11 needs to detect light. Therefore, an area with no metallic wire (i.e. a non-light-blocking area) is formed in the metallic wiring layers 321 to 324 directly above the photodiode 11 to create a window opening 36 consisting of only the substantially tubular interlayer dielectric 33 and protective film layer 34, through which light can reach the photodiode 11. As shown in FIG. 4, incident light coming from above impinges on the photodiode 11 and undergoes a photoelectric conversion by the photodiode 11. In this process, if the incident light should reach the circuit section 31 other than the photodiode 11 or a resistor circuit (not shown) for holding and transferring signals produced by the picture elements, the light would be a noise, which causes a malfunction or deteriorates the picture quality. Accordingly, the metallic wiring layers 32 are designed to cover the areas other than the area that are directly above the photodiode 11, thereby preventing light from reaching unintended areas.

Thus, the metallic wiring layers 32 have the light-blocking function as well as the wiring function. Furthermore, the present embodiment is characterized in that the uppermost layer (i.e. the fourth metallic wiring layer 324) is used as the measurement electrode 15. This differs from the conventional four-level wiring in which the fourth metallic wiring layer 324 is electrically used for supplying power or ground potential and optically used as a light blocker covering a particularly large area that includes not only the photodiode 11 but also other areas. In the image sensor of the present embodiment, as shown in FIG. 4, the fourth metallic wiring layer 324 is divided into small sections according to the pattern of the picture cells 10, and the protective film layer 34 covering the surface of the fourth metallic wiring layer 324 has an opening 35, so that each picture cell 10 has a measurement electrode 15 exposed to the outside. Naturally, this measurement electrode 15 still functions as a light-blocking layer that prevents light from reaching the circuit section 31 and other elements.

As described previously, the fourth metallic wiring layer 324 has a grid-shaped blank area to separate the measurement electrodes 15 of the neighboring picture cells 10. The fourth metallic wiring layer 324 cannot block light in this area. Taking this problem into account, the metallic wiring patterns at the lower layers (i.e. the first to third metallic wiring layers 321 to 323) are designed to protect the blank area, whereby a sufficient degree of light-blocking effect is obtained under that area. Thus, the entire light-blocking effect is ensured.

Thus, in the picture-element structure of the image sensor of the present embodiment, the uppermost (fourth) metallic wiring layer 324, which was conventionally used mainly for the light-blocking purpose, is utilized to provide a measurement electrode 15 in each picture cell 10.

FIG. 5 shows the circuit configuration for one column in the column circuit section 3. There are actually two identical circuits on the left, one of which is for the optical measurement output signal line 25 and the other for the electrical measurement output signal line 26; however, one of them is omitted in the diagram. This output circuit, which is connected to an end of either the optical measurement output signal line 25 or electrical measurement output signal line 26, includes two MOS transistors 40 and 41 connected in series and one MOS transistor 42 functioning as an amplifier. On the other hand, the reset/current-supply circuit, which is connected to an end of the column reset signal line 24, includes a switch section 43, a current/voltage (I/V) conversion amplifier 44, another switch section 45 including a plurality of switches, and a resistor section 46 including a plurality of resistors with different resistances. The switch section 45 and resistor section 46 are to be inserted into the feedback circuit of the amplifier 44.

A measurement process using the image sensor with the previously described configuration is hereinafter described. In the process of acquiring an optical two-dimensional image and electrical two-dimensional image of a specimen by this image sensor, the specimen should be directly placed on the protective film layer 34, which as a whole covers the surface of the image sensor.

In the case of the optical measurement, the photodiode 11 in each picture cell 10 should be reset at the beginning of one cycle (e.g. one frame) for acquiring image signals. In the resetting operation, the switch 43a is on and 43b is off in the column circuit section 3, and a predetermined reset voltage VRS is given to the column resent signal line 24. In this state, a reset signal ORS is applied to the optical measurement reset signal line 20 to turn on the first MOS transistor 12 in the picture cell 10, whereupon the cathode potential of the photodiode 11 is temporarily reset to the aforementioned voltage VRS. Then, when light impinges on the photodiode 11 with the first MOS transistor 12 maintained in the off state, an electric current corresponding to the strength of the received light flows in the photodiode 11, and the photodiode potential gradually decreases due to an electric discharge caused by the electric current. The rate of this potential decrease depends on the strength of the received light; the decrease rate is higher as the received light is stronger.

While the third MOS transistor 14 is in the off state, the second MOS transistor 13 is practically isolated from the optical measurement output signal line 25. When the third MOS transistor 14 is turned on by a selection signal SEL supplied to the row selection signal line 23, an electric current corresponding to the photodiode potential at that time flows through the second MOS transistor 13 functioning as a source follower amplifier and is supplied to the optical measurement output signal line 25. As explained earlier, the rate of decrease in the photodiode potential is higher as the received light is stronger. This means that receiving a larger amount of light during a specified period of time results in a lower photodiode potential.

The current signal supplied to the optical measurement output signal line 25 is converted to a voltage signal by the MOS transistors 41 and 42 functioning as load resistances in the column circuit section 3. Then, this voltage signal is amplified by the MOS transistor 43 and sent to the output circuit section 4. In the output circuit section 4, the row scanner 2 sequentially selects individual columns to be read, whereby a voltage signal corresponding to the picture cell 10 that belongs to the selected column among the m pieces of picture cells 10 constituting one row is sent to the output terminal 7. Thus, the voltage signals each corresponding to the amount of light received by the photodiode 11 of each picture cell 10 are sequentially extracted.

Unlike the optical measurement, the electrical measurement does not require the resetting operation if the measurement is intended for simply measuring the voltage of a target object. With the fourth MOS transistor 16 in the off state, when the sixth transistor 18 is turned on, a current signal corresponding to the potential generated at the measurement electrode 15 flows into the electrical measurement output signal line 26. Then, this current is converted to a voltage signal in the column circuit section 3 and read out through the output circuit section 4.

As a mode of the electric measurement, an electric-current measurement with an electric current being supplied into an object to be observed can be performed by using the column reset signal line 24 as follows. In this measurement, the switch 43b is turned on and 43a is turned off in the column circuit section 3. Then, a predetermined control voltage VCT is applied to the inversion input terminal of the I/V conversion amplifier 44, and one of the switches 45 is turned on to select the gain of the I/V conversion amplifier 44. In this state, when the fourth MOS transistor 16 is turned on, a measurement current passes through the target object being in contact with the measurement electrode 15, by way of the fourth MOS transistor 16, column reset signal line 24, switch 43b, switch section 45 and resistor section 46. The I/V conversion amplifier 44 outputs a voltage signal corresponding to the measurement current.

In this manner, current signals at different control voltages can be concurrently measured with m pieces of measurement electrodes 15 included in the m pieces of picture cells 10 constituting one row.

Second Embodiment

Figure 6:
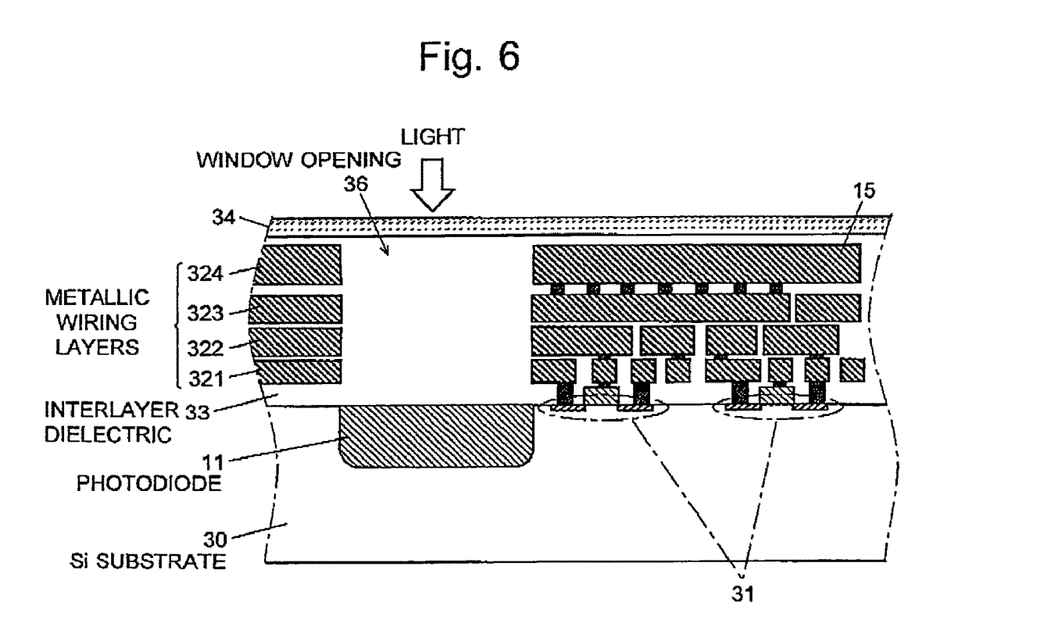
FIG. 6 is a schematic vertical sectional view of one picture cell in an image sensor according to another embodiment (second embodiment) of the present invention.

In the electric measurement with the image sensor of the first embodiment, a voltage signal or current signal was extracted through the measurement electrode 15 being in direct contact with an object to be observed. A minor modification to the structure of the first embodiment enables the device to perform the measurement in an indirect, capacity-coupling mode. FIG. 6 is a vertical sectional view of the picture cell in this (second) embodiment. The cell structure is basically identical to that of the first embodiment shown in FIG. 4. The difference exists in that, unlike the first embodiment in which the measurement electrode 15 was exposed through the opening 35 formed in the protective film layer 34 covering the measurement electrode 15, the second embodiment has the measurement electrode 15 entirely covered with the protective film layer 34.

Similar to the previous case, a specimen to be measured is directly placed on the protective film layer 34. In this state, the measurement electrode 15 is capacity-coupled with the specimen overhead since the protective film layer 34 between the measurement electrode 15 and the specimen is a kind of dielectric. Thus, a potential results between them. In the case of the second embodiment, this potential generated at the measurement electrode 15 is to be extracted through the MOS transistors 17 and 18 to the electric measurement output signal line 26 and externally detected.

Unlike the first embodiment, in the present case it is impossible to pass an electric current through the specimen via the measurement electrode 15. Therefore, the I/V conversion amplifier 44 and its feedback circuit in the column circuit shown in FIG. 5 are unnecessary. By contrast, the resetting operation through the switch section 43 is important.

The reason can be understood by considering the situation where the resetting MOS transistor 16 is tentatively omitted from the circuit shown in FIG. 2. In this case, if electric charges are accumulated at the gate-source/drain junctions of the MOS transistor 17 during an LSI manufacturing process or other stages, those charges may possibly remain in the circuit and cause a background noise because the measurement electrode 15 in the second embodiment is unexposed and therefore cannot provide an escape for those electric charges. To avoid this problem, the device in the second embodiment is designed so that all the measurement electrodes 15 of the picture cells 10 can be reset via the resetting MOS transistor 16 and column reset signal line 24. Thus, the accumulated charges can be removed so that the electrical measurement can be performed with little noise.

Third Embodiment

In the image sensor of the first embodiment, the optical measurement section 10a and electrical measurement section 10b in each picture cell 10 are separately provided. This configuration is advantageous in that the optical and electrical measurements can be performed simultaneously. However, this configuration is disadvantageous to the miniaturization of the picture cell 10 since it requires six MOS transistors for each picture cell 10. The image sensors in the third and fourth embodiments are designed so that the picture cell 10 can be constructed with fewer transistors, although the optical and electrical measurements cannot be simultaneously performed.

Figure 7:
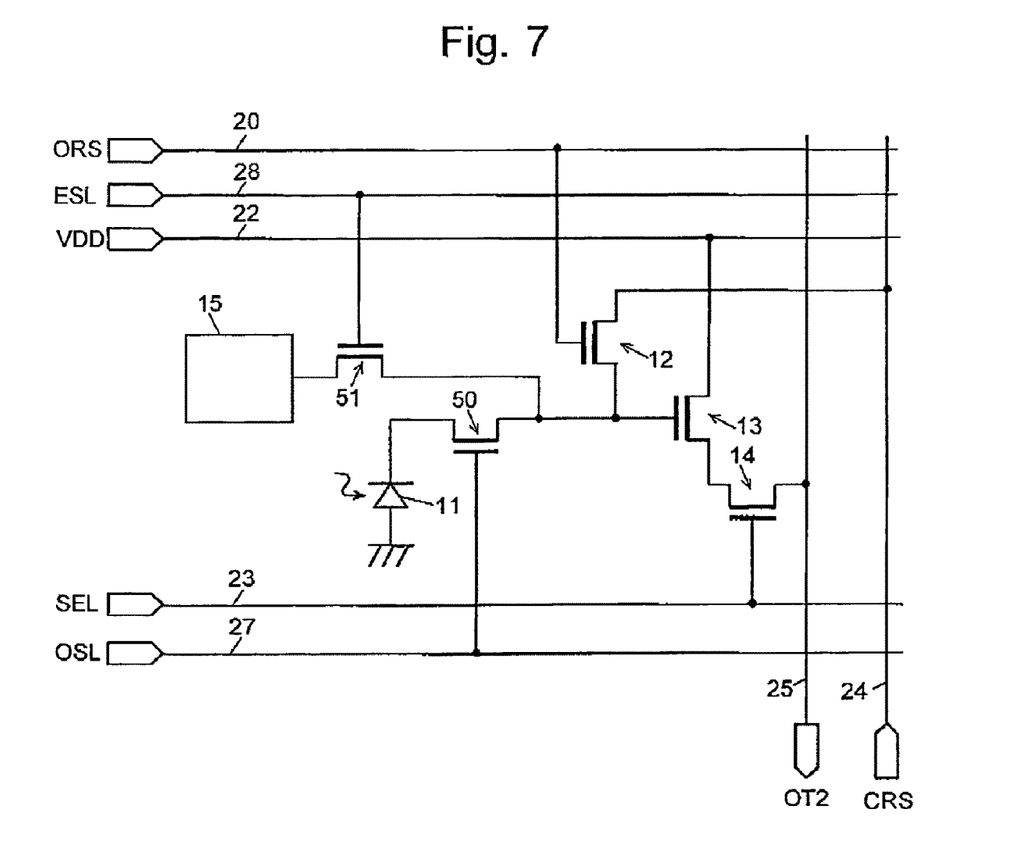
FIG. 7 is a circuit configuration diagram of one picture cell in an image sensor according to another embodiment (third embodiment) of the present invention.

FIG. 7 is a circuit configuration diagram of one picture cell in the image sensor of the third embodiment. In this configuration, the MOS transistors 12 for a resetting operation, 13 as a source follower amplifier and 14 for output selection are shared by the optical and electrical measurements. Furthermore, there is only one output signal line 25. On the other hand, a MOS transistor 50 for selecting the optical measurement mode and a MOS transistor 51 for selecting the electrical measurement mode are provided to allow selection between the optical and electrical measurements. These two MOS transistors have their gate terminals connected to an optical measurement selection signal line 27 and electrical measurement selection signal line 28, respectively.

In this configuration, the MOS transistors 50 and 51 are selectively turned on through the optical measurement selection signal line 27 or electrical measurement selection signal line 28, whereupon either the cathode terminal of the photodiode 11 or the measurement electrode 15 is connected to the MOS transistors 12, 13 and other components, so that the operations necessary for the previously described measurements can be performed.

Fourth Embodiment

Figure 8:
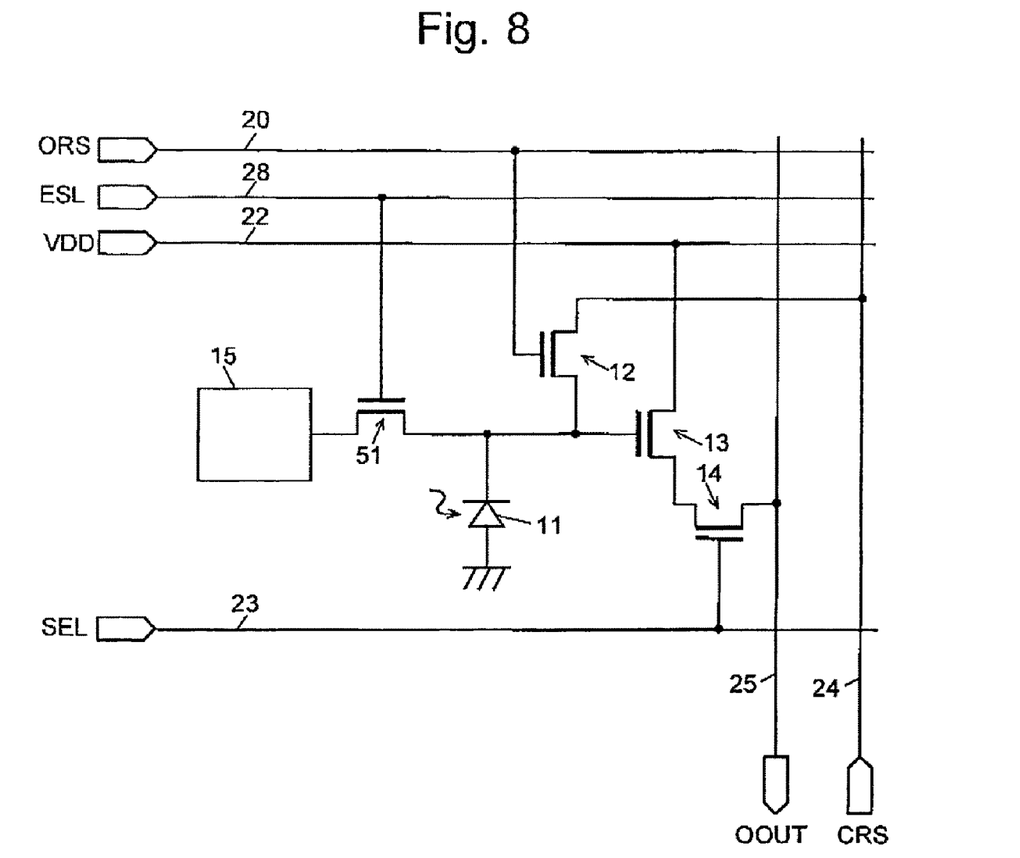
FIG. 8 is a circuit configuration diagram of one picture cell in an image sensor according to another embodiment (fourth embodiment) of the present invention.

FIG. 8 is a circuit configuration diagram of one picture cell in an image sensor of the fourth embodiment. This configuration has been achieved by omitting the MOS transistor 50 from the picture cell 10 in the third embodiment. In this case, when the MOS transistor 51 is in the off state, the measurement electrode 15 is isolated and an optical measurement using the photodiode 11 can be performed. On the other hand, when the MOS transistor 51 is in the on state, the measurement electrode 15 is connected to the gate terminal of the MOS transistor 13, so that an electrical measurement using the measurement electrode 15 can be performed. It should be noted that the photodiode 11 is also connected during this electrical measurement. Accordingly, the electrical measurement should preferably be conducted under the condition that the fluctuation of incident light falling onto the photodiode 11 is negligible.

It is of course possible in the third or fourth embodiment to construct the device as a direct measurement type as in the first embodiment or capacity-coupling measurement type as in the second embodiment.

It should be noted that the preceding embodiments are mere examples, and any changes or modifications appropriately made within the spirit of the present invention will be included in the scope of the claims of this patent application.

The invention claimed is:

1. An image sensor having a semiconductor substrate on which both an optical measurement function for obtaining optical information originating from a specimen and an electrical measurement function for obtaining electrical information due to the specimen via a direct contact or capacity-coupling with the specimen are mounted, comprising:
   a) a photoelectric conversion unit for the optical measurement function, located in a surface layer of the semiconductor substrate;
   b) a plurality of light-blocking layers covering the surface layer of the semiconductor substrate, at least an uppermost layer thereof being an electrically conductive layer having a non-light-blocking area for introducing light into the photoelectric conversion unit; and
   c) measurement electrodes for the electrical measurement function, created by utilizing the uppermost electrically conductive layer of the light-blocking layers.

2. The image sensor according to claim 1, wherein:
   a protective film layer is formed on a surface layer of the light-blocking layers; and
   an opening is formed in the protective film layer above the measurement electrode.

3. The image sensor according to claim 2, wherein a large number of picture cells are arrayed in a two-dimensional pattern with n rows and m columns on one side of the semiconductor substrate, each picture cell including a first readout circuit for selectively reading out an electric signal obtained by the photoelectric conversion unit and a second readout circuit for reading out an electric signal obtained by the measurement electrode, in addition to the photoelectric conversion unit and the measurement electrode.

4. The image sensor according to claim 3, wherein:
   the first readout circuit for the optical measurement and the second readout circuit for the electrical measurement are separately provided for each picture cell; and a signal readout line shared by a plurality of picture cells arranged in a row is separately provided for each of the optical and electrical measurements.

5. The image sensor according to claim 3, wherein:
at least a portion of the first readout circuit is shared with the second readout circuit in each picture cell; and
a signal readout line shared by a plurality of picture cells arranged in a row is used in both the optical and electrical measurements.

6. The image sensor according to claim 3, wherein:
a transistor element for resetting a photodiode as the photoelectric conversion unit is provided in each picture cell; and
the measurement electrode in the same picture cell can be reset by means of the transistor element.

7. The image sensor according to claim 1, wherein:
the measurement electrode is covered with a protective film layer; and
an electric signal is generated in the measurement electrode by capacity-coupling the measurement electrode to the specimen on the protective film layer with the protective film layer in between.

8. The image sensor according to claim 7, wherein a large number of picture cells are arrayed in a two-dimensional pattern with n rows and m columns on one side of the semiconductor substrate, each picture cell including a first readout circuit for selectively reading out an electric signal obtained by the photoelectric conversion unit and a second readout circuit for reading out an electric signal obtained by the measurement electrode, in addition to the photoelectric conversion unit and the measurement electrode.

9. The image sensor according to claim 8, wherein:
the first readout circuit for the optical measurement and the second readout circuit for the electrical measurement are separately provided for each picture cell; and
a signal readout line shared by a plurality of picture cells arranged in a row is separately provided for each of the optical and electrical measurements.

10. The image sensor according to claim 8, wherein:
at least a portion of the first readout circuit is shared with the second readout circuit in each picture cell; and
a signal readout line shared by a plurality of picture cells arranged in a row is used in both the optical and electrical measurements.

11. The image sensor according to claim 8, wherein:
a transistor element for resetting a photodiode as the photoelectric conversion unit is provided in each picture cell; and
the measurement electrode in the same picture cell can be reset by means of the transistor element.

12. The image sensor according to claim 1, wherein a large number of picture cells are arrayed in a two-dimensional pattern with n rows and m columns on one side of the semiconductor substrate, each picture cell including a first readout circuit for selectively reading out an electric signal obtained by the photoelectric conversion unit and a second readout circuit for reading out an electric signal obtained by the measurement electrode, in addition to the photoelectric conversion unit and the measurement electrode.

13. The image sensor according to claim 12, wherein:
the first readout circuit for the optical measurement and the second readout circuit for the electrical measurement are separately provided for each picture cell; and
a signal readout line shared by a plurality of picture cells arranged in a row is separately provided for each of the optical and electrical measurements.

14. The image sensor according to claim 12, wherein:
at least a portion of the first readout circuit is shared with the second readout circuit in each picture cell; and
a signal readout line shared by a plurality of picture cells arranged in a row is used in both the optical and electrical measurements.

15. The image sensor according to claim 12, wherein:
a transistor element for resetting a photodiode as the photoelectric conversion unit is provided in each picture cell; and
the measurement electrode in the same picture cell can be reset by means of the transistor element.

16. The image sensor according to claim 1, wherein the measurement electrodes are arrayed in a two-dimensional pattern with n rows and m columns and designed to collect an electric signal due to the specimen via capacity-coupling, and the image sensor further comprises:
a MOS transistor circuit provided for each measurement electrode, for reading out an electric signal collected through the measurement electrode; and
a MOS transistor circuit provided for each measurement electrode, for resetting a potential accumulated in the measurement electrode.

17. The image sensor according to claim 1, wherein the measurement electrodes are arrayed in a two-dimensional pattern with n rows and m columns and designed to collect an electric signal due to the specimen through capacity-coupling, and the image sensor further comprises:
a readout MOS transistor circuit provided for each measurement electrode, for reacting out an electric signal collected through the measurement electrode;
a current-injection MOS transistor circuit provided for each measurement electrode, for supplying an electric current into the specimen via the measurement electrode; and
a current supply circuit and a current supply line which are separately provided for each column where the current supply line is connected to the current-injection MOS transistor circuits corresponding to a plurality of measurement electrodes arranged in a column.

* * * * *